United States Patent [19]

Enstrom

[11] Patent Number: 4,712,548
[45] Date of Patent: * Dec. 15, 1987

[54] BLOOD LANCING DEVICE

[76] Inventor: Hans Enstrom, Graners Grand 1, S-151 57 Sodertalje, Sweden

[*] Notice: The portion of the term of this patent subsequent to Jun. 30, 2004 has been disclaimed.

[21] Appl. No.: 810,924

[22] Filed: Dec. 19, 1985

Related U.S. Application Data

[63] Continuation-in-part of Ser. No. 541,989, Oct. 14, 1983, Pat. No. 4,676,244, which is a continuation-in-part of Ser. No. 245,080, Mar. 18, 1981, abandoned.

[30] Foreign Application Priority Data

Apr. 23, 1980 [SE] Sweden .................................. 80 03057

[51] Int. Cl.⁴ .............................................. A61B 17/32
[52] U.S. Cl. .................................. 128/314; 128/329 R; 128/315; 30/357
[58] Field of Search .................... 128/314, 315, 329 A, 128/329 R, 305, 753, 754, 763, 770; 30/346.55, 346, 366, 357

[56] References Cited

U.S. PATENT DOCUMENTS

| | | | |
|---|---|---|---|
| 951,309 | 3/1910 | Eskridge | 128/305 |
| 2,919,692 | 1/1960 | Ackermann | 128/329 |
| 3,990,451 | 11/1976 | Gibbs | 128/754 |
| 4,128,351 | 12/1978 | Kurtz et al. | 128/305 |
| 4,185,634 | 1/1980 | Freedman | 128/314 |
| 4,210,145 | 7/1980 | Nestor et al. | 128/305 |
| 4,314,570 | 2/1982 | Sarstedt | 128/763 |
| 4,360,016 | 11/1982 | Sarrine | 128/329 R |
| 4,403,617 | 9/1983 | Tretinyak | 128/754 |
| 4,414,975 | 11/1983 | Ryder et al. | 128/329 R |
| 4,534,827 | 8/1985 | Henderson | 128/305 |
| 4,574,802 | 3/1986 | Straub | 128/305 |
| 4,589,421 | 5/1986 | Ullman | 128/763 |
| 4,602,630 | 7/1986 | Anis | 128/305 |

Primary Examiner—John D. Yasko
Assistant Examiner—Denise Whelton
Attorney, Agent, or Firm—Murray Schaffer

[57] ABSTRACT

A plunger having an oblong body with a front end and a rear end and a lancet having a cutting edge projecting axially from said body at the front end is insertable in a cylinder having an oblong hollow body with a front end, a rear end and an axial hole. The plunger of such a length and the lancet is so arranged that it protrudes a predetermined distance out of the cylinder at the front end when the plunger is inserted thereby defining an operative cutting position. The plunger and cylinder have first engaging stop means arranged after partial insertion of the plunger, to temporarily prevent continued insertion at a predetermined initial position. The arresting function of the stop means is overcome by applying pressure on the plunger thereby pushing it the remaining distance into the cylinder from the initial position to the operative position. The lancet has a single cutting edge extending transversely to the axis of the lancet and a pair of identical inclined surfaces uniformly disposed about the cutting edge.

19 Claims, 10 Drawing Figures

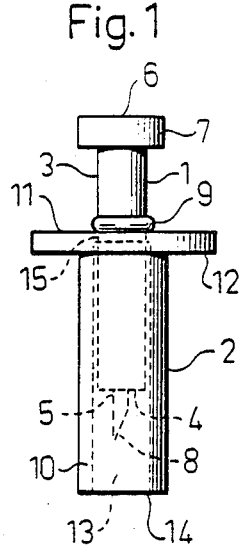
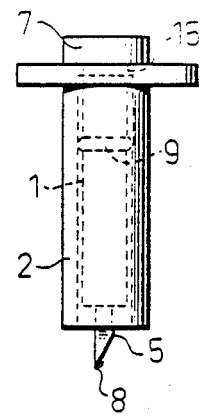
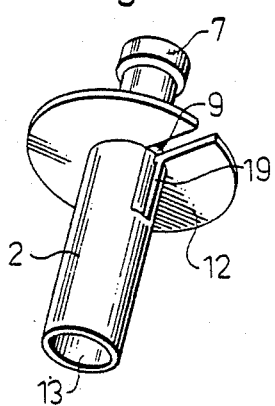
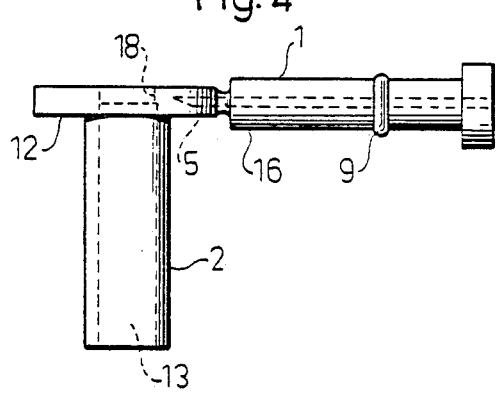
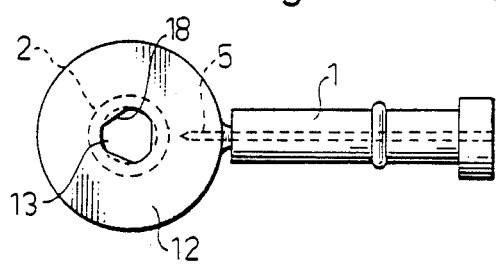
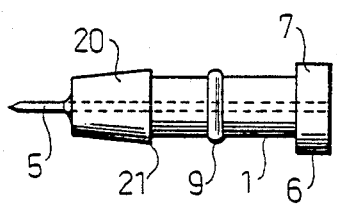

BLOOD LANCING DEVICE

RELATED APPLICATION

The present application is a Continuation-In-Part of co-pending Ser. No. 541,989 filed Oct. 14, 1983 now U.S. Pat. No. 4,676,244 which in turn was a Continuation-In-Part of Ser. No. 245,080 filed Mar. 18, 1981, itself now abandoned.

BACKGROUND OF THE INVENTION

The present invention relates to an improved lancing devicefor effecting bleeding by puncturing the skin of an individual to permit collecting a few drops of blood for diagnostic purposes or the like medical use.

It is known to puncture the skin with a lancet retaining body which is used in combination with a separate mechanical apparatus including a biased striker mechanism and a device to release said striker. The striker mechanism has a support for mounting a lancet retaining body therein. Such an apparatus is expensive to manufacture and time-consuming in use. When the lancet is mounted in the support there is the danger of the sterile lancet being accidently touched with the fingers or other objects with consequent danger of bacterial contamination of the lancet. It is also not possible to make the lancet tip invisible for the patient.

Furthermore, in the known lancets or blood letting devices the puncture is produced by a needle having a pointed tip, which may sometimes have a small bevel for facilitating entry into the shin. In all cases, however, the needle punctures the skin and the underlying tissue, resulting in a hole created by pushing and forcing the tissue radially outward. Such needles produce a small hole through which only a very small amount of blood escapes and results in a severe traumatic effect to both skin and tissue, requiring treatment over an extended period.

It is, therefore, an object of the present invention to provide an improved medical lancet means which can be produced more economically and which can be used more conveniently and safely than previously designed lancets.

It is a further object of the present invention to provide an improved needle for a lancet which produces increased blood flow with reduced traumatic impact.

It is a further object of the present invention to provide a lancing devicewhich does not require packaging in a separate wrapper in order to ensure the sterility thereof and which makes use of all members thereof for the incision including the member that protect the lancet tip.

These and other objects of this invention will become apparent from the detailed description and the claims to follow when read in conjunction with the accompanying drawing.

BRIEF DESCRIPTION OF DRAWINGS

In the drawings:

FIG. 1 is a side view of a lancing device according to the present invention;

FIG. 2 is a side view of the device according to FIG. 1 in operative position when in use;

FIG. 3 is a perspective view of a modified embodiment of the device according to the invention;

FIGS. 4 and 5 are a side view and top view; respectively of another embodiment of a means according to the invention produced as a unit with the lancet unexposed and sterile, but having members which can be separated;

FIG. 6 is a side view of another embodiment of a plunger according to the present invention;

DESCRIPTION OF THE INVENTION

Figure 7:
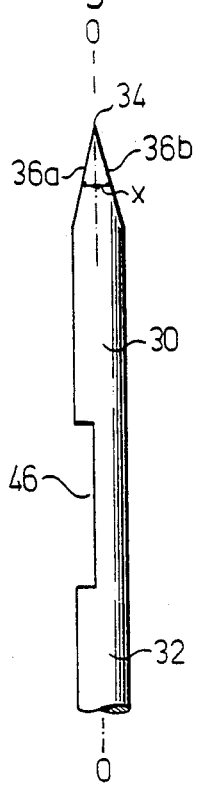
FIG. 7 is a side elevational view of a novel lancet for use in the lancet means of FIGS. 1-6, embodying the present invention.

The improved lancing device shown in the drawings comprises two cooperating members in the form of a male member 1 and a female member 2 both of which preferably being disposable.

The male member comprises an oblong solid, cylindrical rod body 3 having a lancet 5 such as a needle of suitable metal projecting axially from the front end 4 of the rod body and a circular pressure plate 7 formed at the rear end 6 of the rod body. The rod body 3 and the pressure plate 7 are manufactured of suitable plastic material in one piece, while the lancet being preferably separately formed is molded into the rod body 3 at the same time so that it is permanently fixed in the solid rod body and so that a pointed end section 8 thereof projects axially therefrom. Furthermore, the male member 1 carrying the lancet is provided with a circumferential ridge 9 or the like protrusion to temporarily obstruct movement, or some other temporary stop means, the function of which will be explained below.

The female member acting as carrier and guide for the male member comprises an oblong, sleeve-like, open-ended, cylindrical hollow body 10 and a finger-grip plate 12 formed at the rear end 11 of the body. In the embodiment shown, the hollow body 10 has an axial through hole 13 adapted to slidingly receive the rod body 3 of the male member without friction. A slight clearance may be permitted between the parts.

The male and female members are so designed with respect to each other that when the male member is fully inserted in the female member the pointed end section 8 of the lancet will project a predetermined distance, usually about 0.5-2 mm, out of the female member. In this final and puncturing operative position the pressure plate 7 is in contact with the finger-grip plate 12 or rear end 11. The female member is manufactured of suitable plastic material, preferably of the same plastic material as the male member.

The lancing device also comprises first engaging stop means adapted to constrict passage or temporarily obstruct movement, said first stop means comprising a first element aranged on the rod body of the male member at a predetermined distance from the pointed end section 8 of the lancet, and a second element arranged on the female member at a predetermined distance from the front end 14 thereof to engage with said first element. In the embodiment shown said first stop element consists of said radially protruding ridge 9, while the second stop element consists of a corresponding annular radially inwardly extending ridge 15 on the inner wall or at the entry of the hole in the female member. The ridge 15 of the female member thus forms a constriction of the hole 13 at the entry thereof so that continued movement of the male member into the female member is prevented, as is illustrated in FIG. 1, since the ridge 9 engages the protrusion 15 of the female member. By increasing the pressure with the thumb or other finger on the pressure plate 7 of the male member, this stop is finally overcome so that the male member can be inserted the full length determined by the rod body 3 into the female member, as is illustrated in FIG. 2. When this increased pressure is suddenly released by the ridges 9, 15 moving past and out of engagement with each other, the male member acquires an extremely high speed the rest of the distance into the female member until a second engaging stop means are reached. The second stop means comprises the pressure plate 7 of the male member and the rear end 11 of the female member.

The action created by overcoming the first stop means and the sudden arrest at the second stop means causes the pointed end section 8 of the lancet to be pushed out of the female member at a very high speed to rapidly penetrate the skin and the blood vessels beneath. It will be understood that the front end 14 of the female member will be in contact with the skin at least from the point when the pressure is increased on the male member after the temporary engagement of the first stop means has been reached.

In discussing the male and female members 1 and 2 respectively, the ridge 9 on the male member is placed at a specific point on the rod body 3 so that the distance between the ridge 9 and the pointed end section 8 of the lancet is the same as and preferably slightly less than the distance between the front end 14 of the female member and the stop ridge 15. It is thus ensured that the pointed end section 8 of the lancet will not be visible from the side when the first stop means is temporarily in engagement, provided the female member is made of opaque plastic, which is preferred. It is believed that it is of great psychological significance for many patients that the lancet is invisible.

If desired, the female member may be provided with a slit 19 at its rear end 11, to enable the entry to the hole 13 to expand upon application of said pressure on the male member. Such an embodiment is illustrated in FIG. 3.

The lancing device thus described can preferably be made in one piece, the male member and female member being in an integral piece or unit 16 and easily severable from each other at the moment of use. Such a unit is shown in FIGS. 4 and 5. The unit is injection molded so that the pointed end section of the lancet is located in the finger-grip plate 12 of the female member and directed radially therein. A slight twist of the male member will separate this from the female member at the thin and frangible connection 17 which surrounds a small portion of the lancet. The lancet molded in this manner, is completely protected and sterile up to the moment of use. Moreover, such protection is provided by an operative member, i.e. the female member, rather than a separate non functional part. Thus, no special protective element, which must then be disposed, is required.

In the embodiment according to FIGS. 4 and 5, the female member has been provided with three evenly distributed ridges or protrusions 18 cooperating with the protrusion 9 of the male member to form said first stop means. Otherwise, the protrusions act in cooperation with the protrusions 9 in the same manner as the protrusions 15, earlier described, did.

Instead of placing the male and female members in right angle, as shown in FIG. 4, they may be molded to form an oblong unit, the pointed end section of the lancet being enclosed in the frontal face of the finger-grip plate 12 from above and, if necessary, in the rear face, in extra material under the plate. In this manner the male and female members are axially aligned.

The plastic material used for the male and female members is entirely free from foreign substances and is of a quality approved for foodstuffs. Thus, plasticized organic polymeric compositions, such as as polyvinyl chlorida, polyethylene, polypropylene and the like plastic materials, are well suited for molding the medical lancet means. The lancet is made of special stainless steel.

Attachment of the lancet needle in the plunger can be accomplished easily and simply by washing the lancet with alcohol or alcohol solution prior to its automatic insertion in the plastic injection molding tool, without any object have a fat or oily surface coming into contact with the lancet after washing.

To ensure secure accurate molding of the lancet into the male member, the injection molding tool may comprise three radially directed holder elements which support the automatically inserted lancet from two opposite directions, such as from below and above, corresponding radial slits being formed in the molded male member.

The stop means which act last, i.e. said second stop means which are formed in the embodiment shown by the pressure plate 7 of the male member and the rear end 11 of the female member, according to an alternative embodiment may be formed by the front end 4 of the male member and an inner shoulder or ridge in the female member, said shoulder or ridge being formed by a bottom section in the female member, the hole thereof terminating at a distance from the front end of the female member. A narrow central hole is made in said bottom section for passage of the pointed end of the lancet.

According to a further embodiment, shown in FIG. 6, the male member is provided with a device which prevents the male member from falling out of the female member when the lancing device is in its initial position prepared for use. Such a device comprises a plunger 1 which is provided with a conical forward end 20 which is enlarged on its rear so that it forms a circumferential protrusion 21. This protrusion 21 is arranged to engage with either ridge 15 or 18 of the cylinder 2 after the partial insertion of the plunger into the cylinder. The diameter of the protrusion is smaller than that of the ridge 9 but greater than the entrance of the hole 13 in order to engage with the ridge 15 or 18. Thus, the protrusion 21 forms a further stop means which prevents the plunger and lancet from accidentally falling out of the rear end of the cylinder and thereby ensures the sterility of the lancet once it has been removed from its sterile position and made ready for use. A ridge, step or similar stop means may be formed on rod body 3 between front end 4 and ridge 9 in view of a circular protrusion.

An improved lancet which provides improved results from the standpoint of pain, body trauma and the production of blood is the subject of the inventive aspects shown in FIGS. 7-10. In the embodiment seen in FIGS. 7 and 8 a lancet generally depicted by the numeral 3 is provided comprising an elongated shank 32 of sufficient length to be firmly and stably embedded in the plastic material forming the rod body 3 of the male member. The lancet 30 has a single, straight transverse cutting edge 34 situated in a longitudinal central plane passing through the axis 0—0 and a pair of inclined surfaces 36a and 36b of identical size and taper, on each side of the cutting edge. The inclined surfaces encompass an angle X of between 15 to 20 degrees and each surface 36a and 36b has a length of between 0.5 to 1.5 mm, it being preferred that the length be about 1.0 mm.

Instead of punching the skin and tissue resulting in a round hole as in the prior devices which use a needle having a conical pointed end, the new lancet makes a knife-like wide cut in the skin and also in the tissue below the skin so that many blood-vessels will be opened instead of being forced aside as is the case with a pointed needle without any transverse cutting edge. Moreover, the two effective inclined surfaces 36a and 36b force the tissue on both sides of the cut in a direction outwardly from each other creating a large space which is immediately filled with blood when the lancet is withdrawn. The result is that the amount of blood flowing out from the cut will increase considerably. Because the incision in the body of the patient is created by a knife, rather than a punch, the trauma to the body is greatly lessened.

Figure 8:
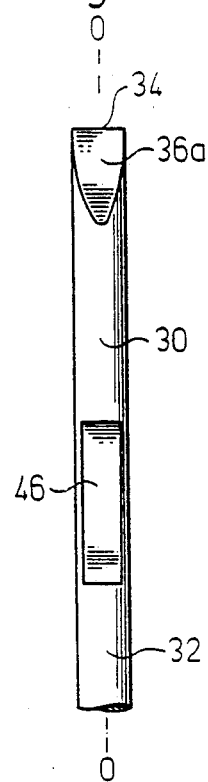
FIG. 8 is a front elevational view of the lancet of FIG. 7.

Since the lancet of FIGS. 7 and 8 acquires a high speed when used in the body previously described the cutting edge will, upon the sudden release and pushing in of the male body member, act as a knife penetrating the skin extremely quickly. It has been found that, thanks to this, the sensation of pain is extremely slight and brief.

Figure 9:
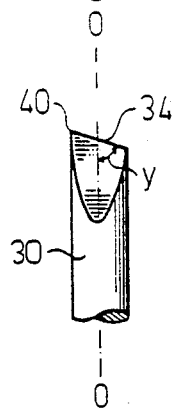
FIG. 9 is partial front elevational view of a lancet formed in accord with another embodiment of the present invention.
Figure 10:
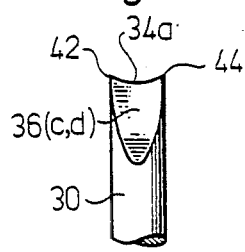
FIG. 10 is another view similar to FIG. 9, showing still another embodiment of the novel lancet.

The straight cutting edge 34 may be perpendicular to the axis 0—0 as seen in FIGS. 7 and 8 or it may be inclined with respect to the axis 0—0 at an angle Y about 75 degrees, so that a leading point 40 is obtained, as seen in FIG. 9. In addition, as seen in FIG. 10 the inclined surfaces 36c and 36d may themselves be concavely formed, thereby forming a cutting edge 34a which is concavely arcuate, providing two leading edges 42 and 44. The embodiments of FIGS. 9 and 10 function generally in the manner described in connection with the embodiment of FIGS. 7 and 8.

As seen in FIGS. 7-10, the lancet 30 is made with a recess or cavity 46 formed in a chordal portion if its shank 32 at a distance from the cutting edges 34 so that it would be normally enclosed in the material forming the plunging rod 3. In this way, the exact orientation and position of the lancet (i.e. cutting edge) relative to the rod axis is assured during the molding with the plastic of the plunger rod. Such orientation cavity 46, is not critical to the structure but only preferable in simplifying assembly and strength against rotative separation from the plastic.

As mentioned, the lancet may consist of a suitable metal. However, it may of course consist of some other suitable material if desired. The lancet may, for instance, consist of a suitable plastic material and according to such an embodiment the lancet is molded as an integral part of the male member, i.e. of the same plastic material.

What I claim is:

1. A disposable miniature lancing device for obtaining a drop of blood by cutting the skin without passing through the body of the patient comprising a cylinder and a plunger, at least said cylinder being formed of a material distendable under force applied thereto, said plunger being insertable at its front end into said cylinder, said plunger and said cylinder having a slight clearance enabling said plunger to be freely slidable within said cylinder, sadi plunger having a radially extending flange at its rear end engageable with the rear end of said cylinder for limiting passage of said plunger throguh said cylinder and defining the full insertion of said plunger in said cylinder, a lancet integrally formed with said plunger and having a cutting edge projecting axially from said front end of said plunger, said plunger, cylinder and lancet being so formed that said lancet protrudes from the front end of said cylinder a predetermined distance when said plunger is fully inserted within said cylinder, said cutting edge extending transversely to said plunger in a longitudinal plane passing through the central axis of said lancet and having a pair of identical inclined surfaces extending on either side of said longitudinal plane freom said cutting edge and forming uniform angles with the central plane.

2. The lancing device according to claim 1 wherein the inclined surfaes encompass an angle of between 15 to 20 degrees.

3. The lancing device according to claim 2 wherein each inclined surface has a length of between 0.5 to 1.5 mm.

4. A lancing device according to claim 2 wherein each inclined surface are concavely formed.

5. The lancing device according to claim 1 wherein said cutting edge extends at an angle to the central axis of said lancet.

6. The lancing device according to claim 5 wherein the cutting edge extends at an angle of 75 degrees.

7. The lancing means according to claim 1 wherein said lancet is provided with a chordal recess set back from said cutting edge and encased in said plunger.

8. The lancing device according to claim 1 wherein the outer surface of said plunger has a radially outwardly protruding peripheral ridge spaced from the rear end thereof and the inner surface of said cylinder has at least one radial projection extending inwardly from the wall adjacent the rear end thereof, said peripheral ridge and projection cooperating to form detent means for restricting the freely slidable movement of said plunger at a predetermined location within said cylinder, said location being less than the full insertion of said plunger so that said lancet remains within said cylinder spaced from the front end thereof, said restriction being overcome by application of an axial force on said plunger at said rear end thereof, said axial force causing said cylinder to distend and the peripheral ridge to pass axially over said projection without fracture of said ridge or projection, said plunger being thereafter freely movable through said cylinder into the fully inserted position.

9. The lancing device according to claim 8, wherein said plunger and cylinder are molded as a unit, said plunger being integrally connected at its forward end to portion of said cylinder, so as to be easily severable said connection being thin and easily frangible permitting severance of said plunger from said cylinder and exposure of the tip of said lancet.

10. The lancing device according to claim 8 wherein the cylinder is formed with a radially exterior flange forming a finger-grip for the user.

11. The lancing device according to claim 8 wherein the cylinder has a slit at said rear end to enable the entrance of the hole to expand upon said application of pressure on the plunger.

12. The lancing device according to claim 8 wherein said lancet protrudes from the front end of said plunger, when fully inserted in said cylinder between 0.5–2 mm.

13. The lancing device according to claim 8 when the entrance to said cylinder at its rear end has radially inward stop means restricting the movement of said plunger, and said plunger is provided with a circumferential protrusion located axially between the peripheral ridge and the front end of the plunger, said circumferential protrusion having a diameter less than that of said peripheral ridge but greater than that of the entrance to said cylinder at the rear end.

14. In a lancing device for obtaining a drop of blood, a needle comprising a solid shank having a cutting edge at one end, said cutting edge extending transversely to said shank in a longitudinal plane passing through the central axis of said lancet and said shank having a pair of identical concave surfaces inclined downwardly on either side of said longitudinal plane from said cutting edge and forming uniform angles with the central plane.

15. The lancing device according to claim 14 wherein the incline of said concave surfaces encompass an angle of between 15 to 20 degrees with the longitudinal plane.

16. The lancing device according to claim 15 wherein each concave surfce has a length of between 0.5 to 1.5 mm.

17. The lancing device according to claim 14 wherein said cutting edge extends at an angle to the central axis of said lancet.

18. The lancing device according to claim 17 wherein the cutting edge extends at an angle of 75 degrees.

19. The lancing means according to claim 14 wherein said lancet is provided with a chordal recess set back from said cutting edge.

* * * * *